United States Patent
Cheng et al.

(10) Patent No.: US 6,753,453 B2
(45) Date of Patent: Jun. 22, 2004

(54) PRODUCTION OF META-DIISOPROPYLBENZENE

(75) Inventors: Jane Chi-Ya Cheng, Bridgewater, NJ (US); William A. Weber, Burlington, NJ (US); Francis S. Bryan, Townsend, DE (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/299,558

(22) Filed: Nov. 19, 2002

(65) Prior Publication Data

US 2004/0097771 A1 May 20, 2004

(51) Int. Cl.[7] ............................................... C07C 4/12
(52) U.S. Cl. ...................................................... 585/475
(58) Field of Search ......................................... 585/475

(56) References Cited

U.S. PATENT DOCUMENTS

| | | | |
|---|---|---|---|
| 3,308,069 A | 3/1967 | Wadlinger et al. | 252/455 |
| 3,780,123 A | 12/1973 | Suggitt | 260/672 |
| 4,439,409 A | 3/1984 | Puppe et al. | 423/328 |
| 4,822,943 A | 4/1989 | Burress | 585/467 |
| 4,826,667 A | 5/1989 | Zones et al. | 423/277 |
| 4,954,325 A | 9/1990 | Rubin et al. | 423/328 |
| 4,962,257 A | 10/1990 | Absil et al. | 585/475 |
| 4,992,606 A | 2/1991 | Kushnerick et al. | 585/467 |
| 5,198,595 A | 3/1993 | Lee et al. | 585/467 |
| 5,236,575 A | 8/1993 | Bennett et al. | 208/46 |
| 5,250,277 A | 10/1993 | Kresge et al. | 423/329.1 |
| 5,329,059 A | * 7/1994 | Marler | 585/475 |
| 5,362,697 A | 11/1994 | Fung et al. | 502/71 |
| 5,557,024 A | 9/1996 | Cheng et al. | 585/467 |
| 5,672,799 A | * 9/1997 | Perego et al. | 585/467 |
| 6,049,018 A | 4/2000 | Calabro et al. | 585/446 |

* cited by examiner

*Primary Examiner*—Thuan D. Dang
(74) *Attorney, Agent, or Firm*—Darryl M. Tyus; Linda A. Kubena

(57) ABSTRACT

A process for the selective production of meta-diisopropylbenzene is disclosed, wherein the process comprises the steps of contacting cumene under disproportionation conditions and in the absence of added benzene with a catalyst comprising a porous crystalline inorganic oxide material having an X-ray diffraction pattern including d-spacing maxima at 12.4±0.25, 6.9±0.15, 3.57±0.07 and 3.42±0.07 Angstrom to produce a disproportionation effluent containing benzene and mixture of diisopropylbenzene isomers, and then recovering from said disproportion effluent a meta-diisopropylbenzene boiling range fraction in which the ratio of meta-diisopropylbenzene to ortho-diisopropylbenzene is in excess of 50 and the total amount of meta-diisopropylbenzene co-boilers excluding ortho-diisopropylbenzene is less than 1 wt % of said fraction.

7 Claims, No Drawings

PRODUCTION OF META-DIISOPROPYLBENZENE

FIELD OF THE INVENTION

This invention is directed to a process for the selective production of meta-diisopropylbenzene (DIPB).

BACKGROUND OF THE INVENTION

Meta-DIPB is an important intermediate in organic synthesis. Thus resorcinol can be prepared by oxidizing meta-DIPB with air and then decomposing the resulting dihydroperoxide with acid. However, although para-DIPB can be separated from a mixture of PIDB isomers by super fractionation, the boiling points of ortho- and meta-DIPB are too close to allow effective separation of meta-DIPB by fractionation. Moreover, ortho-DIPB is not readily oxidized and hence builds up in the production loop, requiring removal as a purge and representing a yield loss. Thus, to be commercially viable, any process for producing meta-DIPB must minimize the production of the ortho-isomer.

Currently, meta-DIPB is manufactured commercially by alkylating cumene with propylene over a homogeneous $AlCl_3$ catalyst. The high activity of the $AlCl_3$ catalyst produces a mixture of DIPB isomers with near equilibrium ortho content. This is advantageous since at equilibrium in the liquid phase between 50 and 150° C. the ratio of meta:ortho DIPB is greater than 100 providing sufficient purity for efficient downstream conversion to resorcinol. Process operation between 50 and 150° C. also results in DIPB products containing less than 1000 ppm of co-boiling n-propylisopropylbenzene impurities. However, corrosion and the need to neutralize, separate and recycle the $AlCl_3$ catalyst, make it difficult to employ.

DIPB can also be produced by separation from the polyalkylated by-product of the alkylation of benzene with propylene to produce cumene. However, DIPB separated from the polyalkylated fraction of current commercial cumene plants is rich in the kinetically preferred para- and ortho-DIPB isomers, making this route of limited use in the synthesis of meta-DIPB, unless the ortho- and para-content is reduced by, for example, isomerization or transalkylation. Transalkylation and isomerization, however, can introduce contaminant n-propylisopropylbenzenes.

Accordingly, there is an outstanding need for a heterogeneous process for producing DIPB rich in the meta-isomer and substantially free of the ortho-isomer and n-propylisopropylbenzenes.

U.S. Pat. No. 4,992,606 discloses a process for preparing short chain ($C_1$–$C_5$) alkylaromatic compounds by alkylation of an aromatic compound, such as benzene and cumene, with a short chain alkylating agent, such as propylene, over the molecular sieve MCM-22. In addition, U.S. Pat. No. 4,962,257 discloses the use of MCM-22 in the disproportionation of toluene to xylenes.

U.S. Pat. No. 5,329,059 discloses a process for the disproportionation of an alkylaromatic compound, wherein the alkyl group has from 1 to about 6 carbon atoms, e.g., cumene, by contacting said compound with catalyst comprising an active form of synthetic porous crystalline MCM-49.

U.S. Pat. No. 4,822,943 discloses a process for the selective production of para-DIPB by reacting cumene and/or benzene whit propylene over the molecular sieve ZSM-12.

U.S. Pat. No. 5,198,595 discloses a process for preparing alkylaromatic compounds by alkylation of an aromatic compound with an alkylating agent having two to eighteen carbon atoms, such as propylene, over mordenite which has been subjected to repeated calcination and acid treatment so as to have a silica/alumina molar ratio of at least 40:1.

U.S. Pat. No. 6,049,018 discloses the porous crystalline material MCM-68 and its use in the alkylation of aromatics with short chain ($C_2$–$C_6$) olefins (for example, the alkylation of benzene with ethylene or propylene to produce ethylbenzene or cumene respectively), the transalkylation of aromatics (for example, the transalkylation of polyethylbenzenes or polyisopropylbenzenes with benzene to produce ethylbenzene or cumene respectively), and the disproportionation of alkylaromatics (for example, the disproportionation of toluene to produce xylenes).

U.S. Pat. No. 3,780,123 discloses the catalytic disproportionation of alkylbenzenes, including cumene, by contacting the alkylbenzene and a sulfide compound with hydrogen mordenite containing a sulfided Group VIII metal. According to Table 1 of U.S. Pat. No. 3,780,123, when mordenite is used to disproportionate cumene in the presence of methyldisulfide as the sulfide compound, the process produces a mixture of DIPB isomers in which the meta:ortho isomer ratio is between 58 and 85 and the product contains 4.4–7.2 wt % n-propylbenzene and 4.4–5.2 wt % of unidentified impurities. As a co-boiler with cumene, n-propylbenzene is an undesirable impurity, particularly since, on disproportionation, it yields n-propylisopropylbenzenes which tend to co-boil with meta-DIPB.

It will, of course, be understood that the disproportionation of cumene to produce DIPB and benzene is the inverse of the transakylation of DIPB with benzene to produce cumene.

According to the invention, it has now been found that the disproportionation of cumene over MCM-22 and related molecular sieve catalysts is unexpectedly more selective towards the production of the production of meta-DIPB and less selective towards the production of ortho-DIPB than the alkylation of cumene with propylene over the same catalysts. Moreover, such molecular sieve catalysts produce relatively low concentrations of undesirable by-products, particularly compounds coboiling with meta-DIPB, when used in the disproportionation of cumene.

SUMMARY OF THE INVENTION

In one aspect, the invention resides in a process for the selective production of meta-diisopropylbenzene, said process comprising the steps of contacting cumene under disproportionation conditions and in the absence of added benzene with a catalyst comprising a porous crystalline inorganic oxide material having an X-ray diffraction pattern including d-spacing maxima at 12.4±0.25, 6.9±0.15, 3.57±0.07 and 3.42±0.07 Angstrom to produce a disproportionation effluent containing benzene and a mixture of diisopropylbenzene isomers, and then recovering from said disproportionation effluent a meta-diisopropylbenzene boiling range fraction in which the ratio of meta-diisopropylbenzene to ortho-diisopropylbenzene is in excess of 50 and the total amount of co-boilers excluding ortho-diisopropylbenzene is less than 1 wt % of said fraction.

Preferably, the porous crystalline inorganic oxide material is selected from the group consisting of MCM-22, PSH-3, SSZ-25, MCM-36, MCM49, MCM-56, ITQ-1 and ITQ-2.

Preferably, said disproportionation conditions include a temperature of about 100° C. to about 300° C., a pressure of about 20 to about 5000 psig, a WHSV of about 0.01 to about 100 and a hydrogen to hydrocarbon molar ratio of 0 (no hydrogen added) to about 5.

More preferably, said disproportionation conditions include a temperature of about 140° C. to about 220° C., a pressure of about 20 to about 500 psi, a WHSV of about 0.1 to about 10 and a hydrogen to hydrocarbon molar ratio of 0 to about 5.

Preferably, said disproportionation effluent also contains para-diisopropylbenzene and triisopropylbenzenes which are separated from said disproportionation effluent and recycled to said contacting step to produce additional meta-diisopropylbenzene.

Preferably, said process comprises the initial steps of alkylating benzene with propylene to produce an alkylation effluent comprising cumene and then using at least part of the cumene in said alkylation effluent as the feed to said contacting step.

Preferably, at least part of the benzene produced by said contacting step is recycled to the alkylating step.

DETAILED DESCRIPTION OF THE INVENTION

The present invention provides a process for the selective production of meta-diisopropylbenzene by contacting cumene under disproportionation conditions and in the absence of added benzene with a catalyst comprising a porous crystalline inorganic oxide material having an X-ray diffraction pattern including d-spacing maxima at 12.4±0.25, 6.9±0.15, 3.57±0.07 and 3.42±0.07 Angstrom. The contacting step disproportionates at least part of the cumene to produce a disproportionation effluent which contains benzene and a mixture of diisopropylbenzene isomers, in which the ratio of meta-diisopropylbenzene to ortho-diisopropylbenzene is in excess of 50 and the total amount of meta-diisopropylbenzene co-boilers (excluding meta- and ortho-diisopropylbenzene) is less than 1 wt % of said fraction.

Suitable porous crystalline inorganic oxide materials for use in the catalyst of the invention MCM-22, PSH-3, SSZ-25, MCM-36, MCM-49, MCM-56, ITQ-1 or ITQ-2. MCM-22 is described in U.S. Pat. No. 4,954,325, PSH-3 is described in U.S. Pat. No. 4,439,409, SSZ-25 is described in U.S. Pat. No. 4,826,667, MCM-36 is described in U.S. Pat. No. 5,250,277, MCM-49 is described in U.S. Pat. No. 5,236,575; MCM-56 is described in U.S. Pat. No. 5,362,697; ITQ-1 is described in U.S. Pat. No. 6,077,498; and ITQ-2 and its use is described in International Pat. Publication Nos. WO97/17290 and WO01/21562. The entire contents of each of the aforementioned patents are incorporated herein by reference.

The porous crystalline inorganic oxide material used in the process of the invention does not contain the sulfided hydrogenation metal disclosed in U.S. Pat. No. 3,780,123.

As in the case of many catalysts, it may be desirable to incorporate the porous crystalline inorganic oxide material used in the catalyst of the invention with another component resistant to the temperatures and other conditions employed in cumene disproportionation. Such components include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a component which is active tends to change the conversion and/or selectivity of the catalyst in the disproportionation process. Inactive components suitably serve as diluents to control the amount of conversion in the process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline inorganic oxide material include the montmorillonite and kaolin family, which families include the subbentonites, aid the kaolins commonly known as Dixie, McNamee, Georgia and Florida clays or others in which the main mineral constituent is halloysite, kaolinite, dickite, nacrite, or anauxitec. Such clays can be used in the raw state as originally mined or initially subjected to calcination, acid treatment or chemical modification. Binders useful for compositing with the present crystal also include inorganic oxides, such as silica, zirconia, titania, magnesia, beryllia, alumina, and mixtures thereof.

In addition to the foregoing materials, the porous crystalline inorganic oxide material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of porous crystalline inorganic oxide material and inorganic oxide matrix vary widely, with the crystal content ranging from about 1 to about 90 percent by weight and more usually, particularly when the composite is prepared in the form of beads, in the range of about 2 to about 80 weight percent of the composite.

The conditions used in the process of the invention should be such as to effect significant disproportionation of the cumene in the feed while minimizing the production of by-products, particularly n-propylisopropylbenzenes and triisopropylbenzenes and other heavy materials. Suitable conditions include a temperature of about 100° C. to about 300° C., a pressure of about 20 to about 5000 psig, a WHSV of about 0.01 to about 100 and a hydrogen to hydrocarbon molar ratio of 0 (no hydrogen added) to about 50. More preferably, the conditions include a temperature of about 140° C. to about 220° C., a pressure of about 20 to about 500 psig and WHSV of about 0.1 to about 10 and a hydrogen to hydrocarbon molar ratio of about 0 to about 5. Most preferably, the temperature employed in the process of the invention is from about 150° C. to about 180° C.

The feed to the process of the invention can contain 75 to 100% by weight of cumene and preferably at least about 90% by weight of cumene. The feed should be substantially free of benzene so is to minimize unwanted side reactions, such as transalkylation of benzene with the DIPB product. The feed is also free of added sulfide, such as the methyldisulfide disclosed in U.S. Pat. No. 3,780,123. In particular, the feed can be cumene purchased on the open market or, more preferably, is the direct product of a commercial cumene plant in which benzene is alkylated with propylene over a suitable catalyst. One particularly preferred embodiment uses the product or a slip-stream of a commercial cumene plant in which the benzene alkylation step is conducted in the presence of an alkylation catalyst comprising a molecular sieve catalyst selected from zeolite beta, MCM-22, PSH-3, SSZ-25, MCM-36, MCM49, MCM-56, ITQ-1 or ITQ-2 to produce an alkylation effluent comprising cumene and polyisopropylbenzenes. The cumene is recovered from the alkylation effluent and the polyisopropylbenzenes are separated and fed to a transalkylation unit in which they are converted to additional cumene by transalkylation with benzene in the presence of transalkylation catalyst selected from zeolite beta, mordenite, MCM-22, PSH-3, SSZ-25, MCM-36, MCM49, MCM-56, ITQ-1 or ITQ-2. Zeolite beta is described in U.S. Pat. No. 3,308,069, the entire contents of which is incorporated herein by reference.

The products of the disproportionation process of the invention are benzene and a mixture of DIPB isomers, in which the weight ratio of meta-DIPB:ortho-DIPB is greater than 50. Impurity levels in the product are very low, with the amount of meta and ortho-DIPB coboilers, such as n-propylisopropylbenzenes, being less than 1 wt %, the n-propylbenzene content being less than 1 wt % and preferably less than 0.5 wt %, the TIPB content being less than 5 wt % and preferably less than 1 wt %, and the total content of disproportionation products other than benzene and DIPB being less than 5 wt % and preferably less than 2wt %. Thus by separating a meta-diisopropylbenzene boiling range fraction from the disproportionation effluent, a product can be obtained in which the ratio of meta-diisopropylbenzene to ortho-diisopropylbenzene is in excess of 50 and the total amount of co-boilers excluding ortho-diisopropylbenzene is less than 1 wt % or said fraction The benzene coproduced with the DIPB in the process of the invention is relatively free of co-boiling impurities and hence it can be separated, for example, by distillation, and sold as extraction grade benzene. Alternatively, where the cumene feed is produced by an initial benzene alkylation step, the benzene produced in the process of the invention can be separated and recycled to the alkylation reactor.

The DIPB product of the process of the invention typically contains about 40–70% by weight of the meta isomer and 30–60% by weight of the para-isomer. The individual DIPB isomers can be separated by any convenient means, such as by super-fractionation. If, however, it is required to increase the yield on one of these isomers, say the meta-isomer, it is possible to recycle some or all of the other isomer, say the para-isomer, to the disproportionation reactor, where the para-DIPB will be isomerized to produce the meta -isomer with little or no co-production of the ortho-isomer.

The invention will now be more particularly described with reference to the following Examples. In the Examples, the cumene employed was chemical grade cumene that had been purified by percolation over activated alumina.

EXAMPLE 1

(Comparative): Alkylation of Cumene Over MCM-22

2 g of MCM-22 (1/16" extrudates with 35% alumina binder) were used to alkylate cumene with commercial grade propylene. The catalyst was diluted with about 2 g of sand and charged to a down-flow fixed bed stainless steel reactor having an outside diameter of 3/8". The catalyst was dried at 125° C. and 1 atmosphere pressure with 100 cc/min flowing $N_2$ for 2 hours. While retaining the $N_2$ flow, the reactor pressure was set to 850 psig by a grove loader and the reactor temperature was adjusted to the desired temperature for the first set of alkylation conditions (140° C.). The feed, containing benzene and propylene in the molar ratio stated in Table 1, was introduced to the reactor at the WHSV stated in Table 1. After lining out for 24 hours, liquid products were collected in a cold-trap and analyzed off-line with an HP 5890 gas chromatograph GC. The catalyst was tested at several conditions, with each condition being lined out for 24 hours before collecting a liquid product. Results are shown in Table 1.

TABLE 1

| Conditions | | | | | | |
|---|---|---|---|---|---|---|
| Temperature (C) | 140 | 160 | 180 | 160 | 200 | 220 |
| Pressure (psig) | 900 | 900 | 900 | 900 | 900 | 900 |
| WHSV (1/Hr) | 2 | 2 | 2 | 2 | 2 | 2 |
| Cumene/Propylene (molar) | 4 | 4 | 4 | 4 | 4 | 4 |
| Reactor Effluent (Wt. %) | | | | | | |
| C5-hydrocarbons | 0.0% | 0.1% | 0.1% | 0.1% | 0.0% | 0.4% |
| Benzene | 0.4% | 0.2% | 2.5% | 1.0% | 10.8% | 11.4% |
| EB | 0.0% | 0.0% | 0.0% | 0.0% | 0.0% | 0.2% |
| Cumene | 85.5% | 73.4% | 61.5% | 71.3% | 48.1% | 42.8% |
| C9–C10 Aromatics | 0.0% | 0.0% | 0.0% | 0.0% | 0.0% | 0.5% |
| 1,3-DIPB | 6.1% | 10.1% | 16.9% | 11.0% | 23.9% | 25.7% |
| 1,2-DIPB | 0.3% | 0.5% | 0.5% | 0.4% | 0.3% | 0.3% |
| 1,4-DIPB | 6.9% | 14.1% | 16.7% | 14.7% | 13.7% | 13.3% |
| C10+ Aromatics | 0.1% | 0.3% | 0.3% | 1.2% | 0.0% | 0.9% |
| TIPB | 0.6% | 1.4% | 1.5% | 0.3% | 3.1% | 4.4% |
| Para Selectivity | 51.8% | 57.2% | 49.1% | 56.1% | 36.2% | 34.0% |
| Meta Selectivity | 45.6% | 40.8% | 49.6% | 42.2% | 63.0% | 65.4% |
| Cumene Conversion | 6.5% | 18.5% | 30.5% | 20.6% | 43.8% | 49.1% |
| Benzene/DIPB | 0.06 | 0.01 | 0.16 | 0.08 | 0.59 | 0.60 |
| meta/ortho DIPB ratio | 17.6 | 20.3 | 36.8 | 24.7 | 74.6 | 97.2 |

EXAMPLE 2

Disproportionation of Cumene Over MCM-22

Following the procedure outlined in Example 1, chemical grade cumene was flowed over MCM-22 in the absence of propylene to disproportionate to diisopropylbenzenes (and triisopropylbenzenes) and benzene. Conditions and results were as shown in Table 2.

TABLE 2

| Conditions | | | |
|---|---|---|---|
| Temperature (C) | 240 | 220 | 220 |
| Pressure (psig) | 900 | 900 | 900 |
| WHSV (1/Hr) | 2 | 2 | 1 |
| Reactor Effluent (Wt. %) | | | |
| C5– | 0.1% | 0.1% | 0.0% |
| Benzene | 18.3% | 14.5% | 17.8% |
| EB | 0.2% | 0.0% | 0.0% |
| Cumene | 47.9% | 57.5% | 51.9% |
| C9–C10 Aromatics | 0.7% | 0.2% | 0.2% |
| 1-3DIPB | 19.3% | 16.2% | 17.8% |
| 1-2DIPB | 0.2% | 0.2% | 0.2% |

TABLE 2-continued

| | | | |
|---|---|---|---|
| 1-4DIPB | 10.0% | 9.6% | 9.7% |
| C10+ Aromatics | 1.0% | 0.4% | 0.5% |
| TIPB | 2.3% | 1.3% | 1.8% |
| Para Selectivity | 33.8% | 36.8% | 35.0% |
| Meta Selectivity | 65.4% | 62.3% | 64.3% |
| Cumene Conversion | 52.1% | 42.5% | 48.1% |
| Benzene/DIPB | 1.29 | 1.16 | 1.34 |
| meta/ortho DIPB ratio | 83.1 | 67.6 | 84.9 |

From the data in Tables 1 and 2, it will be seen that propylation of cumene over MCM-22 at temperatures below 180° C. produces DIPB with a significantly lower meta/ortho ratio (less than 25) than that obtained by cumene disproportionation over the same catalyst (68–85). Moreover, although the meta/ortho ratio increases as the alkylation temperature is increased to 180° C. and above, it will be seen from Table 1 that this is accompanied by a significant increase in the amount of co-produced benzene. Since the benzene in the alkylation product is the result of the competing disproportionation reaction, the higher meta/ortho ratio at higher alkylation temperatures is further evidence of the enhanced meta-selectivity of disproportionation over MCM-22.

The data in Table 2 not only demonstrate the advantageous meta-selectivity of MCM-22 as a cumene disproportionation catalyst, but also clearly show that the disproportionation product contains very small amounts of impurities, such as TIPB. It is believed that further increases in the meta-ortho selectivity can be realized by operating at lower disproportionation temperatures, such as 150–180° C.

What we claim is:

1. A process for the selective production of meta-diisopropylbenzene, said process comprising the steps of containing cumene under disproportionation conditions and in the absence of added benzene with a catalyst comprising a porous crystalline inorganic oxide material having an X-ray diffraction pattern including d-spacing maxima at 12.4±0.25, 6.9±0.15, 3.57±0.07 and 3.42±0.07 Angstrom, wherein said porous crystalline inorganic oxide material is selected from the group consisting of MCM-22, PSH-3, SSZ-25, MCM-36, MCM-56, ITQ-1, and ITQ-2 to produce a disproportionation effluent containing benzene and a mixture of diisopropylbenzene isomers, and then recovering from said disproportionation effluent a meta-diisopropylbenzene boiling range fraction in which the ratio of meta-diisopropylbenzene to ortho-diisopropylbenzene is in excess of 50 and the total amount of meta-diisopropylbenzene co-boilers excluding ortho-diisopropylbenzene is less than 1 wt % of said fraction.

2. The process of claim 1, wherein said disproportionation conditions include a temperature of about 100° C. to about 300° C., a pressure of about 20 to about 5000 psig, a WHSV of about 0.01 to about 100 and a hydrogen to hydrocarbon molar ratio of 0 (no hydrogen added) to about 50.

3. The process of claim 1, wherein said disproportionation conditions include a temperature of about 140° C. to about 220° C., a pressure of about 20 to about 500 psig, a WHSV of about 0.01 to about 10 and a hydrogen to hydrocarbon molar ratio of about 0 to about 5.

4. The process of claim 3, wherein said disproportionation conditions include a temperature of about 150° C. to about 180° C.

5. The process of claim 1, wherein said disproportionation effluent also contains para-diisopropylbenzene and triisopropylbenzenes which are separated from said disproportionation effluent and recycled to said contacting step to produce additional meta-diisopropylbenzene.

6. The process of claim 1, and comprising the initial steps of alkylating benzene with propylene to produce an alkylation effluent comprising cumene and then using at least part of said alkylation effluent as the feed to said contacting step.

7. The process of claim 6, wherein at least part of the benzene produced by said contacting step is recycled to the alkylating step.

* * * * *